United States Patent
Ivan

(10) Patent No.: US 11,931,082 B2
(45) Date of Patent: Mar. 19, 2024

(54) SURGICAL INSTRUMENTS WITH COMPLIANT DISTAL STUD CONNECTION

(71) Applicant: Zimmer, Inc., Warsaw, IN (US)

(72) Inventor: William J. Ivan, Woodbridge, NJ (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 17/738,854

(22) Filed: May 6, 2022

(65) Prior Publication Data

US 2022/0361929 A1    Nov. 17, 2022

Related U.S. Application Data

(60) Provisional application No. 63/187,147, filed on May 11, 2021.

(51) Int. Cl.
*A61B 17/72* (2006.01)
*A61B 17/16* (2006.01)
*A61B 17/00* (2006.01)

(52) U.S. Cl.
CPC .......... *A61B 17/725* (2013.01); *A61B 17/164* (2013.01); *A61B 2017/00862* (2013.01)

(58) Field of Classification Search
CPC ........ A61B 17/72–7291; A61B 17/164; A61B 17/92–921
See application file for complete search history.

(56) References Cited

U.S. PATENT DOCUMENTS 9,801,735 B2 * 10/2017 Klepač .................. A61F 2/4684
10,799,249 B2 * 10/2020 Dees ....................... A61B 17/17
2009/0248024 A1 * 10/2009 Edwards ............ A61B 17/1739
606/62
2010/0312244 A1 * 12/2010 Edwards ............ A61B 17/1739
606/62
2013/0150858 A1 * 6/2013 Primiano ........... A61B 17/1675
623/20.35
2013/0172892 A1 * 7/2013 Servidio ............ A61B 17/1662
623/18.11
2013/0325019 A1 * 12/2013 Thomas ............. A61B 17/1764
606/88
2014/0276837 A1 * 9/2014 Chaney ................ A61B 17/155
606/88
2014/0276858 A1 * 9/2014 Major .................. A61B 17/157
606/88
2017/0202584 A1 * 7/2017 Hientzsch .............. A61B 17/72
2018/0168664 A1 * 6/2018 Dees .................... A61B 17/1659
2022/0202464 A1 * 6/2022 Rossney ................. A61B 17/72

* cited by examiner

*Primary Examiner* — Eduardo C Robert
*Assistant Examiner* — Steven J Cotroneo
(74) *Attorney, Agent, or Firm* — SCHWEGMAN LUNDBERG & WOESSNER, P.A.

(57) ABSTRACT

An orthopedic instrument for insertion of an orthopedic device into an intramedullary canal of a bone is disclosed. The orthopedic instrument can include an elongate post and a stud. The post can have a longitudinal axis and can extend along the longitudinal axis between a first end portion and a second end portion. The stud can be connected to the post along a portion of a longitudinal length thereof comprising a first end part, A second part of the stud can be free to elastically deflect laterally with respect to the longitudinal axis when subjected to a bending load and return to a first position when unloaded.

14 Claims, 5 Drawing Sheets

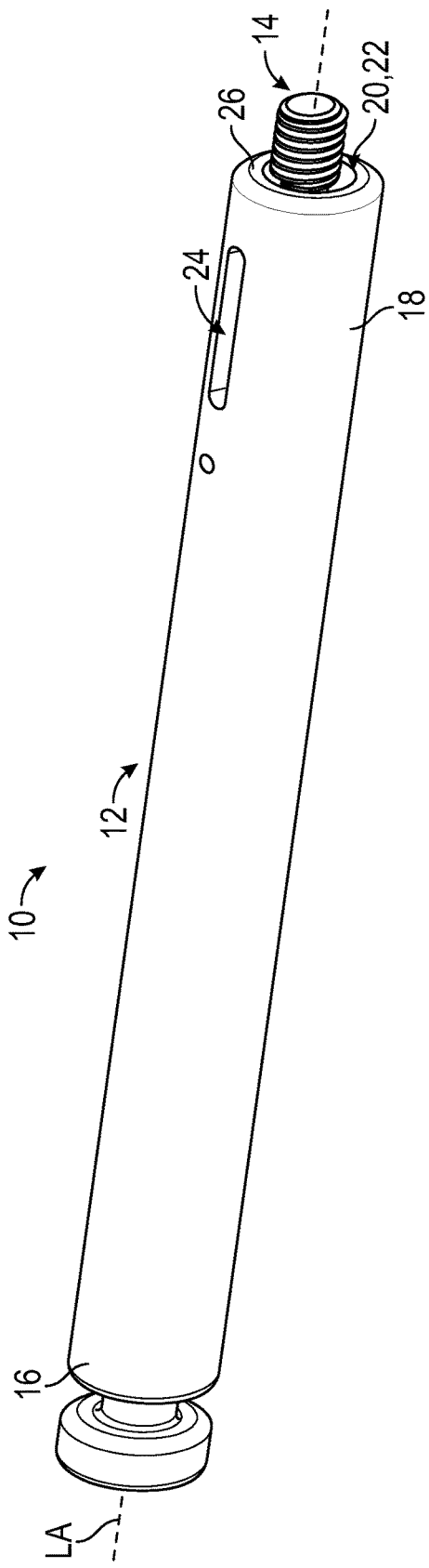
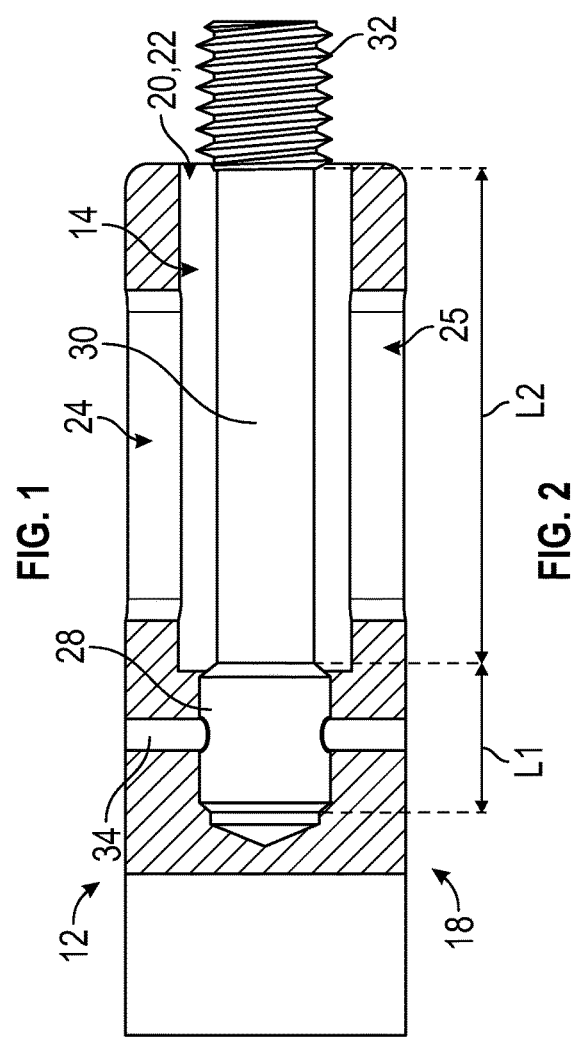
FIG. 1
FIG. 2

SURGICAL INSTRUMENTS WITH COMPLIANT DISTAL STUD CONNECTION

CLAIM OF PRIORITY

This application claims the benefit of U.S. Provisional Patent Application Ser. No. 63/187,147, filed on May 11, 2021, the benefit of priority of which is claimed hereby, and which is incorporated by reference herein in its entirety.

TECHNICAL FIELD

This document pertains generally, but not by way of limitation, to surgical instruments. More specifically, but not by way of limitation, the present application relates to adding a compliant component such as a threaded stud as part of a surgical instrument for coupling the surgical instrument with another instrument, provisional component or a prosthetic implant device.

BACKGROUND

Prosthetic implant devices, such as femoral and tibial components, sometimes include a stem extending from a bearing component such as a tibial tray. The stem can extend along a length of the diaphysis portion of the tibia, while the tray can be configured to abut a resected portion of the epiphysis portion of the tibia configured to mate with the femur. Sometimes the metaphysis portion of the tibia below the epiphysis includes damaged or unhealthy cancellous bone at the resection. As such, it is sometimes desirable to remove weakened bone material, such as with a broach or reamer, to leave a space in the metaphyseal portion of the bone larger than the stem.

Provisional components are temporary components inserted into the bone or joint space. These provisional components used to simulate the size and fit of prosthetic implant devices to ensure selection of a proper prosthetic implant device. A stem provisional component is used to insure a properly sized stem is selected for insertion into the bone such the intermedullary canal thereof. The stem provisional component is typically inserted into place using a surgical tool such as a post.

The present inventor has recognized, among other things, that a problem to be solved can include surgical instruments due to their elongate length and the shape of the bone they are being inserted into can be subject to a bending load. For example, manipulation of the surgical instrument during use while encountering resistance due to the shape of the bone and/or angle of force application can result in loading (bending) on joints or connections such as a connection between the surgical instrument and an orthopedic device (a stem provisional, cutting tip, driver tip, or another component).

According to one specific example, an intramedullary post having an elongate length can be threaded to a stem provisional. The stem provisional in turn can be anchored within the intramedullary canal of a long bone such as a tibia or femur. A cannulated broach is slid over the post and the post serves as a guide for controlling a trajectory of the broach. The broach can be repeatedly driven into an irregular defect in a metaphysis resulting in a well-defined cavity that accepts a trabecular metal implant with a similar shape. In rare cases, due to the factors discussed above, a connection between the post and the stem provisional can plastically bend or even fracture as a result of bending load.

The present subject matter can help provide a solution to this problem, such as by providing a compliant dedicated component, such as a stud, as a connector between the surgical instrument and the orthopedic device. The stud can be compliant in that it can be configured to elastically deflect laterally relative to a longitudinal axis of the post under a bending load but can be configured to return to a first position (e.g., aligned (coincident) or substantially aligned with the longitudinal axis) once unloaded. The stud can be configured to deflect elastically as deflection can be limited by contact between the stud and the post or another component. For example, the post can include a recess at an end portion. At least a portion of the stud can be anchored within the recess. A second portion of the stud can extend freely in a cantilever manner within the recess. Internal surfaces that form the recess comprise walls that can limit deflection of the stud along the second portion to a range where only elastic defection occurs. In this manner, a likelihood of plastic deformation and/or facture of the connection between the surgical instrument and the orthopedic device can be reduced.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

FIG. 1 is a perspective view of an orthopedic instrument comprising an elongate post and a stud according to one example of the present application.

FIG. 2 is a cross-sectional view of an end portion of the post of FIG. 1 showing the stud positioned within a recess in the post according to an example of the present application.

Figure 3A:
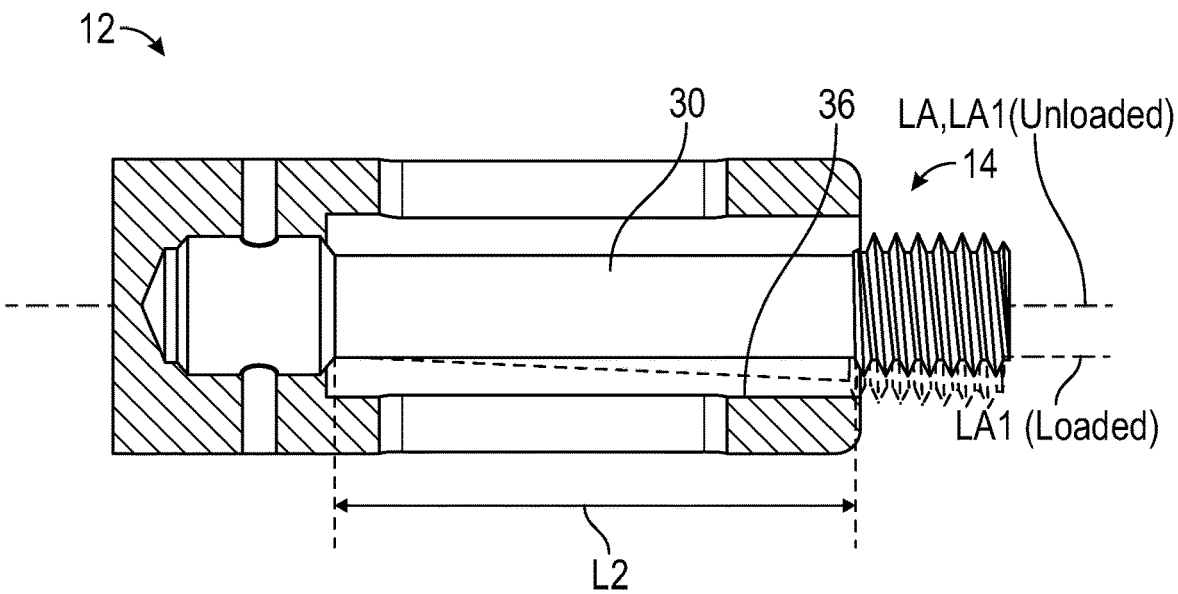
FIGS. 3A and 3B are cross-sectional views of the end portion of the post of FIG. 2 showing the stud flexing from a first position to a second position relative to a longitudinal axis of the post due to application of a bending load thereon according to an example of the present application.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

FIG. 1 is a perspective view of a surgical instrument 10 including a post 12 or shaft and a stud 14. Although described herein in reference to a specific example of the post 12 and the stud 14 for use in an orthopedic knee procedure, the present application contemplates use of the stud with various surgical instruments for various orthopedic procedures that utilize shafts, posts or have tools with an elongate length where a bending load is a concern for causing plastic deflection or failure of a component. As shown in the example of FIG. 1, the post 12 can have an elongate length along a longitudinal axis LA. The post 12 can include a first end portion 16, a second end portion 18, a recess 20, a first opening 22 and a second opening 24.

The first end portion 16 can comprise a proximal portion of the post 12 during the orthopedic procedure as further described herein. The first end portion 16 can include a first end of the post 12. The second end portion 18 can oppose the first end portion 16 and can include a second end 26 of the post 12.

The recess 20 can be configured to receive at least a portion of the stud 14 therein. The first opening 22 can be to the recess 20 and can be located at the second end 26. The recess 20 can comprise a counterbore in the post 12. A portion of the stud 14 can project from the first opening 22. Thus, the stud 14 can form a tip of the surgical instrument 10. The second opening 24 can be through an outer surface of the post 12 at the second end portion 18. The second opening 24 can be spaced from the second end 26. The second opening 24 can communicate with the recess 20 as further illustrated and described.

FIG. 2 is cross-sectional view of the second end portion 18 of the post 12 showing this section and the stud 14 (not shown in cross-section) in further detail. The stud 14 can include a first end part 28 and a second part 30. The second part 30 can include a thread 32. FIG. 2 shows a pin 34 that can be utilized according to some examples. The pin 34 can extend generally laterally through the post 12 and through the first end part 28 of the stud 14.

FIG. 2 shows the first opening 22, the second opening 24 and a third opening 25. The second opening 24 and the third opening 25 can communicate with the recess 20 in a lateral manner with respect to the longitudinal axis LA (FIG. 1) of the post 12.

Figure 4:
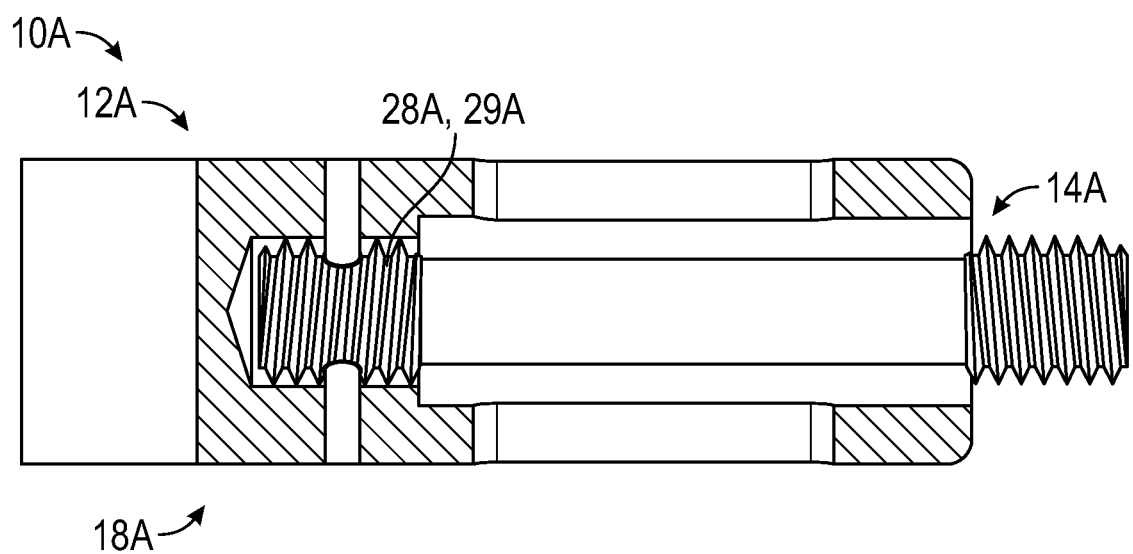
FIG. 4 is a cross-sectional view of an end portion of a post showing a stud threaded into a recess in the post according to another example of the present application.

The stud 14 can have an elongate length with a longitudinal axis. This longitudinal axis of the stud 14 can align or generally align with the longitudinal axis LA of the post 12 (FIG. 1) when the stud is in an unloaded state. The first end part 28 can connect with the second part 30. The first end part 28 can connect with a reduced diameter portion of the post 12 within the recess 20 via a press-fit connection as shown in FIG. 2. However, other types of connection are contemplated including a threaded connection as shown in FIG. 4. The first end part 28 can include a portion of a longitudinal length L1 of the stud 14. Thus, the first end part 28 can be connected to the post 12 along the portion of the longitudinal length L1 thereof rather than simply at an end of the stud 14. The second part 30 can extend freely within the recess 20 and can be anchored such as in a cantilever manner by only the first end part 28. The second part 30 can have a longitudinal length L2 that can vary as desired. A diameter of the second part 30 can be smaller than the first end part 28, for example. The diameter of the second part 30 can be smaller than a diameter of the recess 20. The second part 30 can be free of connection to the post 12. Features of the stud 14 such as the length L2 and the diameter of the second part 30 relative to the diameter of the recess 20 can allow the stud 14 freedom to elastically deflect laterally with respect to the longitudinal axis of the post 12 when subjected to a bending load and return to a first position when unloaded as further discussed and illustrated herein.

The thread 32 can be located on the second part 30 that extends from the recess 20. However, according to other examples the thread 32 could extend into the recess 20 or can be located entirely within the recess 20. According to further examples, the thread 32 can be a female thread rather than the male thread shown in FIG. 2.

Figure 3B:
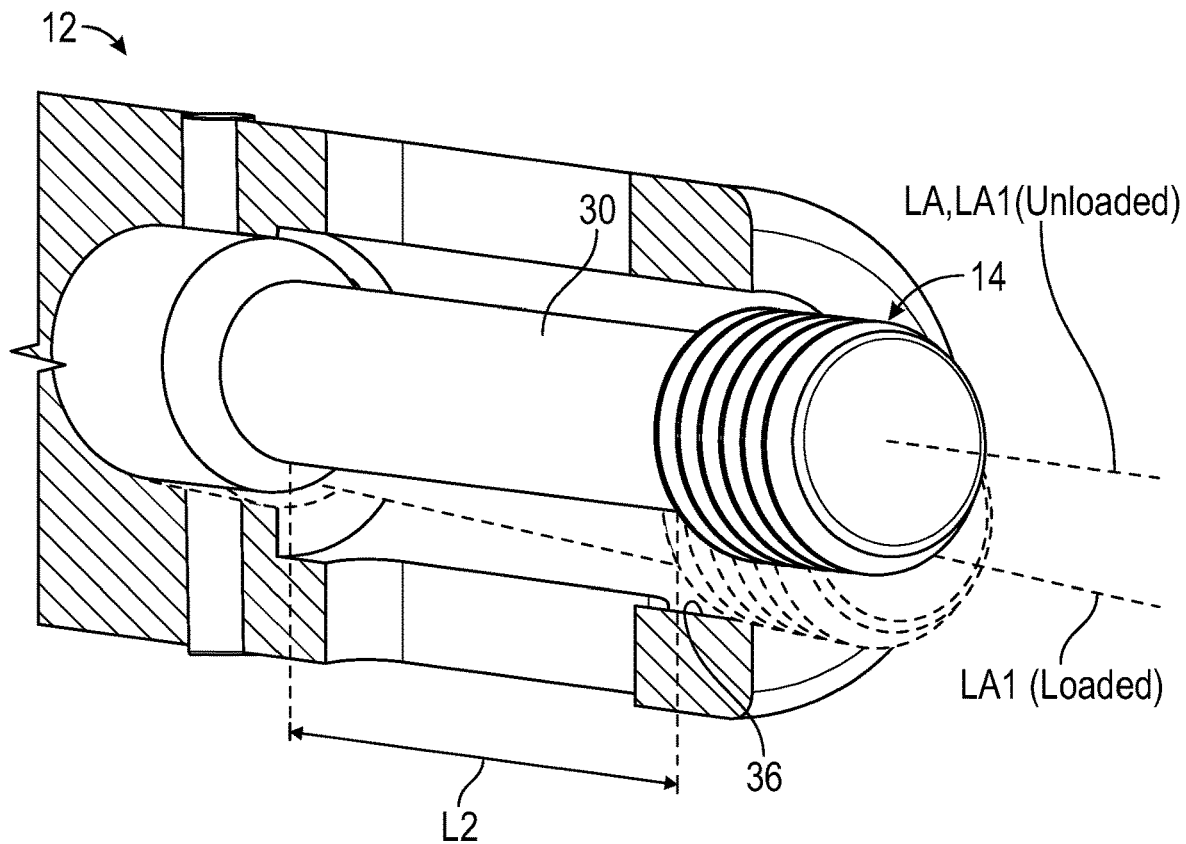

FIGS. 3A and 3B show the stud 14 in a first (unloaded) state where a longitudinal axis LAI of the stud 14 can be aligned (coincident) or generally aligned with the longitudinal axis LA of the post 12. FIGS. 3A and 3B show the stud 14 in a second (loaded) state where the stud 14 is elastically flexed such that the longitudinal axis LA 1 of the stud 14 does not align or generally align with the longitudinal axis LA of the post 12 for all, part or a majority of the longitudinal length L2.

The stud 14 can be limited to an elastic range of deflection by a combination of the longitudinal length L2 but also the relative size of the diameter of the second part 30 as compared with a diameter of the recess 20. An interior surface 36 of the post 12 that defines the recess 20 can limit a distance the stud 14 defects as shown in FIGS. 3A and 3B.

It is contemplated in some examples the post 12 may not include the recess 20. Rather, an addition component; feature or extension of the post 12 can limit deflection of the stud 14 to the elastic range as desired.

FIG. 4 shows an alternative example of a surgical instrument 10A with a cross-sectional view of a second end portion 18A of a post 12A thereof. As shown in the example of FIG. 4, the stud 14A can have a first end part 28A with a thread 29A for connection with a mating thread of the post 12A. In all other respects, the surgical instrument 10A can be constructed in the manner of surgical instrument 10 as previously discussed.

Figure 5C:
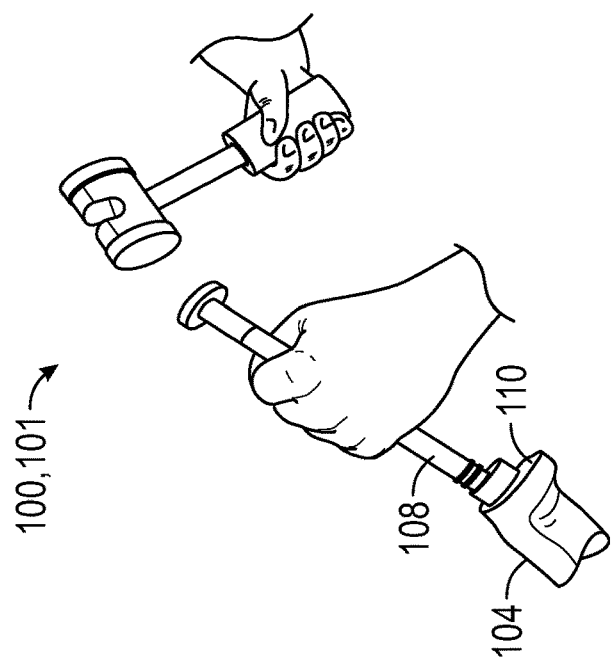
FIGS. 5A-5C illustrates several steps in a method of preparing a bone for receiving a prosthetic device in according to an example of the present application.
Figure 5B:
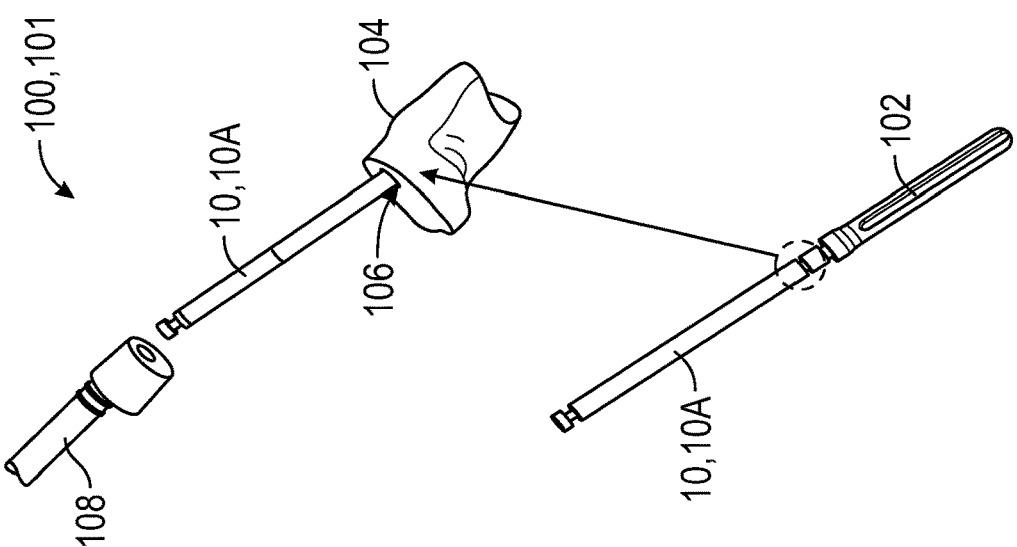
Figure 5A:
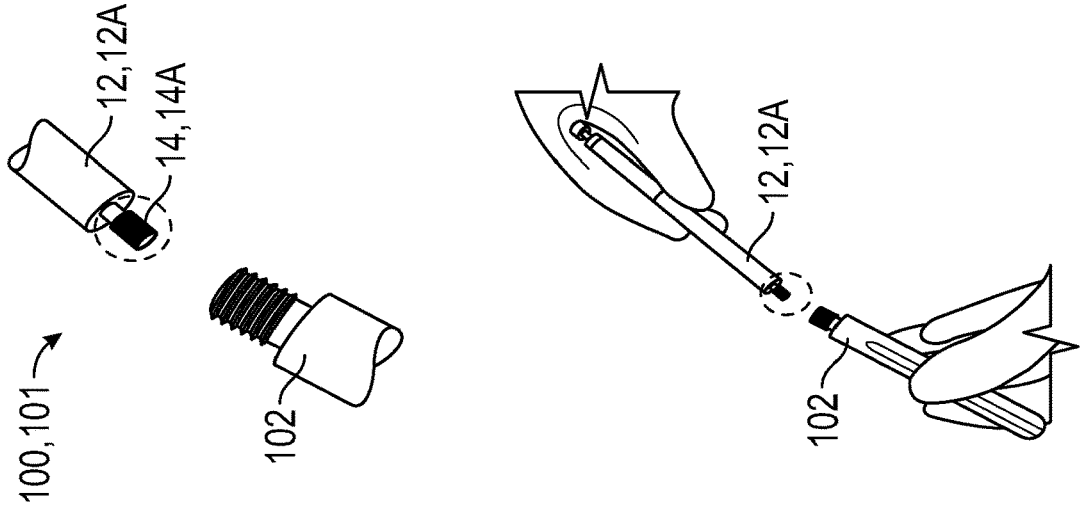

FIGS. 5A-5C shows part of a method 100 and system 101 of implanting a prosthetic device such as a stem provisional 102 in a bone 104 (FIGS. 5B and 5C). The method 100 can include coupling the stem provisional 102 to an elongate post (e.g., 12 or 12A) via a stud (e.g., 14 or 14A). The stud can comprise a component separate from the post. The stud can be configured to defect laterally with respect to a longitudinal axis of the post when subjected to a bending load. FIG. 5A shows the coupling of the stem provisional 102 to the post (e.g., 12 or 12A) via the stud (e.g., 14 or 14A). FIG. 5B shows the assembly of the stem provisional 102 and surgical instrument (e.g., 10 or 10A) with the stem provisional 102 being inserted into a channel 106 in the bone 104 using the post (e.g., 12 or 12A). FIG. 5C shows broaching the channel with a broach 108 guided by the surgical instrument (e.g., 10 or 10A) to form a broached recess in the bone 104 extending to a distance below a planar resected surface 110 of the bone 104.

Figure 6:
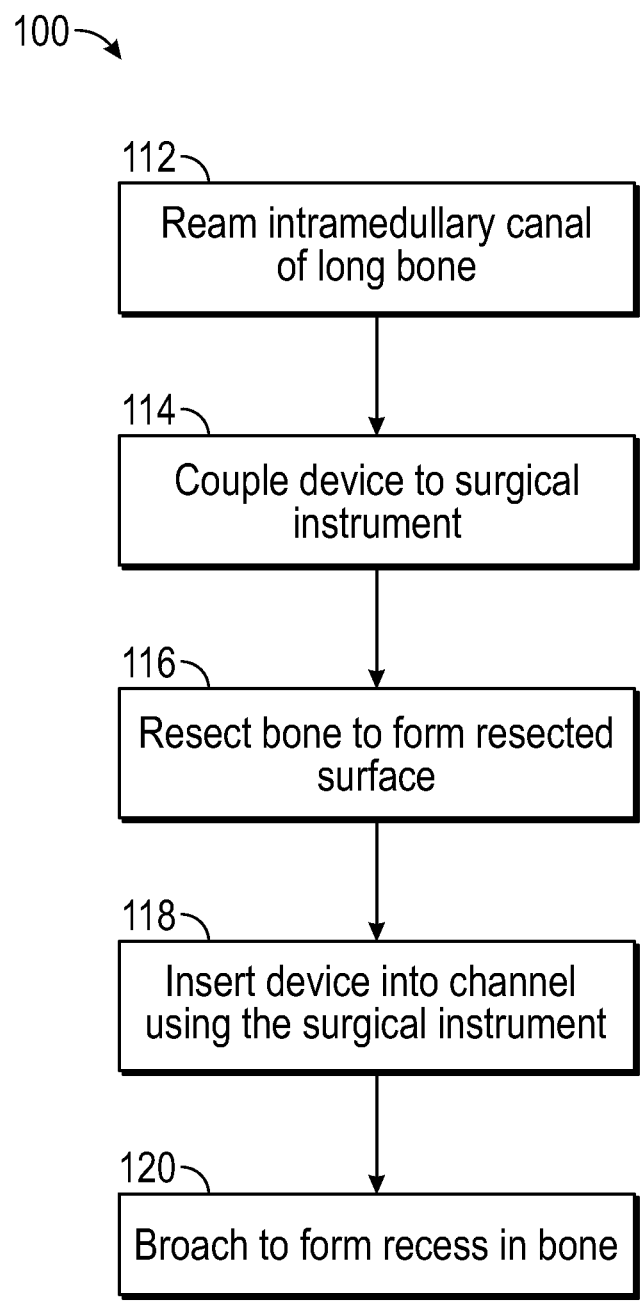
FIG. 6 is a flow diagram of the method of preparing a bone for receiving the prosthetic device.

FIG. 6 shows the method 100 with further steps. The method 100 can temporarily implant a stem provisional in bone. The method 100 can include reaming 112 an intramedullary canal of a bone to form a channel. The method 100 can include coupling 114 the stem provisional to the elongate post via the stud as previously illustrated and described. The method 100 can include resecting 116 the bone to form in a planar resected surface. The method 100 can include inserting 118 the stem provisional into the channel using the post. The method 100 can include broaching 120 the channel to form a broached recess in the bone extending to a distance below the planar resected surface.

VARIOUS NOTES & EXAMPLES

Example 1 is an orthopedic instrument for insertion of an orthopedic device into an intramedullary canal of a bone. The orthopedic instrument can include an elongate post and a stud. The post can have a longitudinal axis and can extend along the longitudinal axis between a first end portion and a second end portion. The stud can be connected to the post along a portion of a longitudinal length thereof comprising a first end part. A second part of the stud can be free to elastically deflect laterally with respect to the longitudinal axis when subjected to a bending load and return to a first position when unloaded.

Example 2 is the orthopedic instrument of Example 1, wherein the stud can be connected to the post at the first end part within a recess in the post and the second part of the stud can be positioned in the recess and can be free to deflect laterally with respect to the longitudinal axis within the recess.

Example 3 is the orthopedic instrument of Example 2, wherein a portion of the second part of the stud can extend from an opening at a second end of the second end portion of the post.

Example 4 is the orthopedic instrument of Example 3, wherein the portion of the second part can be threaded for attachment to the orthopedic device.

Example 5 is the orthopedic instrument of any one of Examples 2-4, wherein the post can define one or more openings that communicate generally laterally with the recess.

Example 6 is the orthopedic instrument of any one of Examples 2-5, wherein an interior surface of the post that defines the recess can limit a distance the stud deflects.

Example 7 is the orthopedic instrument of any one of Examples 1-6, wherein the first end part of the stud can be connected to the post by one of a press-fit or a thread connection.

Example 8 is the orthopedic instrument of Example 7, further optionally comprising a pin extending generally laterally through the post and the first end part of the stud.

Example 9 is an orthopedic system that can include a stem provisional, an elongate post and a stud. The stem provisional can be configured for insertion into an intramedullary canal of a bone. The elongate post can have a longitudinal axis. The post can extend between a first end portion and a second end portion. The second end portion can have a recess therein. The stud can be configured to be inserted within the recess. The stud can be configured to connect to the post at a first end part within the recess. The second part of the stud can extend freely within the recess.

Example 10 is the orthopedic system of Example 9, wherein the second part of the stud can be free to deflect laterally within the recess with respect to the longitudinal axis when connected to the post when subjected to a bending load.

Example 11 is the orthopedic system of Example 10, wherein an interior surface of the post that forms the recess can limit a distance the stud deflects.

Example 12 is the orthopedic system of any one of Examples 9-11, further optionally comprising a broach configured to seat down over the post and remove portions of the bone.

Example 13 is the orthopedic system of any one of Examples 9-12, wherein a part of the stud can extend from the recess and this part can be threaded to attach with the stem provisional. Example 14 is the orthopedic system of any one of Examples 9-13, wherein the first end part of the stud can be configured to connect to the post by one of a press-fit or a thread connection.

Example 15 is the orthopedic system of Example 14, further optionally comprising a pin configured to insert generally laterally through the post and the first end part of the stud.

Example 16 is the orthopedic system of any one of Examples 9-15, wherein the post can define one or more openings that communicate generally laterally with the recess.

Example 17 is a method of temporarily implanting a stem provisional in bone. The method can include any one or any combination of reaming an intramedullary canal of the bone to form a channel, coupling the stem provisional to an elongate post via a stud, wherein the stud comprises a component separate from the post and the stud is configured to defect laterally with respect to a longitudinal axis of the post when subjected to a bending load, resecting the bone to form a planar resected surface, inserting the stem provisional into the channel using the post, and broaching the channel to form a broached recess in the bone extending to a distance below the planar resected surface.

Example 18 is the method of Example 17, wherein the coupling the stem provisional to the elongate post via the stud can optionally include threading the stud into the stem provisional.

Example 19 is the method of any one of Examples 17-18, wherein the stud can be connected to the post by one of a press-fit or a thread connection.

Example 20 is the method of Example 19, wherein the stud can be connected to the post by a pin inserted generally laterally through the post and the stud.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the tel ins "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed. Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An orthopedic instrument for insertion of an orthopedic device into an intramedullary canal of a bone comprising:
   an elongate post having a longitudinal axis, the post extending between a first end portion and a second end portion along the longitudinal axis; and
   a stud connected to the post along a portion of a longitudinal length thereof comprising a first end part; wherein a second part of the stud is free to elastically deflect laterally with respect to the longitudinal axis when subjected to a bending load and return to a first position when unloaded, wherein the stud is connected to the post at the first end part within a recess in the post and the second part of the stud positioned in the recess is free to deflect laterally with respect to the longitudinal axis within the recess, wherein a portion of the second part of the stud extends from an opening at a second end of the second end portion of the post, and wherein the portion of the second part is threaded for attachment to the orthopedic device.

2. The orthopedic instrument of claim 1, wherein the post defines one or more openings that communicate generally laterally with the recess.

3. The orthopedic instrument of claim 1, wherein an interior surface of the post that defines the recess limits a distance the stud deflects.

4. The orthopedic instrument of claim 1, wherein the first end part of the stud is connected to the post by one of a press-fit or a thread connection.

5. The orthopedic instrument of claim 4, further comprising a pin extending generally laterally through the post and the first end part of the stud.

6. An orthopedic system comprising:
   a stem provisional configured for insertion into an intramedullary canal of a bone;
   an elongate post having a longitudinal axis, the post extending between a first end portion and a second end portion, wherein the second end portion has a recess therein; and
   a stud configured to be inserted within the recess, wherein the stud is configured to connect to the post at a first end part within the recess, wherein a second part of the stud extends freely within the recess, wherein the second part of the stud is free to deflect laterally within the recess with respect to the longitudinal axis when connected to the post and when subjected to a bending load, and wherein a part of the stud extends from the recess and this part is threaded to attach with the stem provisional.

7. The orthopedic system of claim 6, wherein an interior surface of the post that forms the recess limits a distance the stud deflects.

8. The orthopedic system of claim 6, further comprising a broach configured to seat down over the post and remove portions of the bone.

9. The orthopedic system of claim 6, wherein the first end part of the stud is configured to connect to the post by one of a press-fit or a thread connection.

10. The orthopedic system of claim 9, further comprising a pin configured to insert generally laterally through the post and the first end part of the stud.

11. The orthopedic system of claim 6, wherein the post defines one or more openings that communicate generally laterally with the recess.

12. A method of temporarily implanting a stem provisional in bone, the method comprising:
   reaming an intramedullary canal of the bone to form a channel;
   coupling the stem provisional to an elongate post via a stud, wherein the stud comprises a component separate from the post and the stud is configured to defect laterally with respect to a longitudinal axis of the post when subjected to a bending load, wherein the coupling the stem provisional to the elongate post via the stud includes threading the stud into the stem provisional;
   resecting the bone to form a planar resected surface;
   inserting the stem provisional into the channel using the post; and
   broaching the channel to form a broached recess in the bone extending to a distance below the planar resected surface.

13. The method of claim 12, wherein the stud is connected to the post by one of a press-fit or a thread connection.

14. The method of claim 13, wherein the stud is connected to the post by a pin inserted generally laterally through the post and the stud.

* * * * *

UNITED STATES PATENT AND TRADEMARK OFFICE
CERTIFICATE OF CORRECTION

PATENT NO. : 11,931,082 B2
APPLICATION NO. : 17/738854
DATED : March 19, 2024
INVENTOR(S) : William J. Ivan It is certified that error appears in the above-identified patent and that said Letters Patent is hereby corrected as shown below:

On the Title Page

Item [57], Line 8, delete "part," and insert --part.-- therefor

In the Claims

In Column 7, Line 30, in Claim 1, delete "part;" and insert --part,-- therefor

Signed and Sealed this
Twenty-eighth Day of May, 2024

*Katherine Kelly Vidal*
Katherine Kelly Vidal
*Director of the United States Patent and Trademark Office*